United States Patent
Lee et al.

(10) Patent No.: US 10,877,009 B2
(45) Date of Patent: Dec. 29, 2020

(54) PARTICLE MEASURING SYSTEM

(71) Applicant: HCTM CO., LTD., Gyeonggi-do (KR)

(72) Inventors: Hongku Lee, Gyeonggi-do (KR);
Cheolhong Kim, Seoul (KR);
Jeongsuk Choi, Gyeonggi-do (KR);
Youngmin Seo, Gyeonggi-do (KR)

(73) Assignee: HCTM CO., LTD., Gyeonggi-do (KR)

( * ) Notice: Subject to any disclaimer, the term of this patent is extended or adjusted under 35 U.S.C. 154(b) by 104 days.

(21) Appl. No.: 16/277,981

(22) Filed: Feb. 15, 2019

(65) Prior Publication Data
US 2020/0132645 A1   Apr. 30, 2020

(30) Foreign Application Priority Data
Oct. 31, 2018   (KR) .................. 10-2018-0131710

(51) Int. Cl.
*G01N 33/00* (2006.01)
*G01N 15/02* (2006.01)

(52) U.S. Cl.
CPC ..... *G01N 33/0016* (2013.01); *G01N 15/0211* (2013.01)

(58) Field of Classification Search
CPC .................. G01N 33/0016; G01N 15/0211
USPC ................................................ 73/31.02
See application file for complete search history.

(56) References Cited

U.S. PATENT DOCUMENTS

| | | | | |
|---|---|---|---|---|
| 3,765,771 A * | 10/1973 | Shaw | ................... | G01N 15/065 377/10 |
| 7,499,809 B2 * | 3/2009 | Nagura | .............. | G01N 15/0211 702/29 |
| 2003/0133111 A1 * | 7/2003 | Yamaguchi | ........ | G01N 15/1456 356/336 |
| 2005/0028957 A1 * | 2/2005 | Suistomaa | ............. | G01N 21/85 162/198 |
| 2008/0152547 A1 * | 6/2008 | Hopke | ................... | G05D 23/24 422/109 |
| 2008/0239283 A1 * | 10/2008 | Tamura | ................... | G01N 15/06 356/36 |
| 2010/0090041 A1 * | 4/2010 | Pejcinovic | ............... | G01N 1/04 241/69 |
| 2015/0330886 A1 * | 11/2015 | Ho | ...................... | G01N 15/0266 356/336 |

FOREIGN PATENT DOCUMENTS

KR   10-1606561   3/2016

* cited by examiner

*Primary Examiner* — Max H Noori
(74) *Attorney, Agent, or Firm* — Ladas & Parry, LLP

(57) ABSTRACT

A particle measuring system including two drying units. One drying unit serves to dry fine particles, and the other drying unit serves to regenerate a dehumidifying agent. The dehumidifying agent is regenerated and used semi-permanently without being replaced with a replacement and is used more conveniently without the inconvenience of a dehumidifying agent replacing operation. The continuity and accuracy of a measurement result is improved.

8 Claims, 5 Drawing Sheets

PARTICLE MEASURING SYSTEM

CROSS-REFERENCE TO RELATED APPLICATION

This application claims the priority to Korean Patent Application No. 10-2018-0131710 filed in the Korean Intellectual Property Office on Oct. 31, 2018, the entire content of which is incorporated herein by reference.

BACKGROUND

Field

The present disclosure relates to a particle measuring system and, more particularly, to a particle measuring system including two drying unit units, in which one drying unit serves to dry fine particles, and the other drying unit serves to regenerate a dehumidifying agent, so that the dehumidifying agent can be regenerated and used semi-permanently without being replaced with a replacement and may be used more conveniently without the inconvenience of a dehumidifying agent replacing operation, and the continuity and accuracy of a measurement result can be improved.

Description

In general, in a nano-level high-precision process, such as semiconductor processing or liquid crystal display (LCD) processing, pollutant particles occurring in operating equipment may result in fatal defects in products. Thus, processing is performed in clean and controlled equipment, such as a clean room, so that a high-degree of cleanliness can be maintained. With such clean equipment, real-time monitoring of pollutant particles is performed very strictly.

Accordingly, such equipment is provided with a particle measuring system for measuring pollutant particles in the equipment. States of distribution of particles in specific chambers of the equipment are measured in real-time by the particle measuring system.

The particle measuring system measures states of distribution of particles, i.e. sizes and numbers of particles, in a specific measurement chamber. The particle measuring system is used in a variety of fields, other than in that of clean rooms, to measure states of distribution of air pollutant particles or to measure the state of distribution of specific particles in laboratories.

In particular, active research into fine particles as air pollutant particles is actively underway. Fine particles generate ultrafine particles, as well as ozone acting as a cause of secondary pollutants, through atmospheric chemical reaction in the air. In addition, fine particles from vehicle emissions may contain a large amount of carcinogens. Such fine particles can penetrate deep into lung cells without being filtered through the respiratory tract or by mucous membranes. Fine particles can move to the brain and may be easily accumulated in the human body. Accordingly, fine particles threaten human health in a variety of manners.

To accurately measure and research various types of fine particles as described above, particle measuring systems have been widely used to date. In general, fine particles absorb trace amounts of moisture present in the air or are easily coagulated by moisture. Accordingly, a particle measuring system must be provided with a drying unit able to dry fine particles in order to accurately measure fine particles.

A drying unit of a particle measuring system is configured to dry fine particles in a variety of manners. For example, the drying unit may dry fine particles in the form of aerosols by heating fine particles together with ambient air or may dry fine particles in the form of aerosols by dispersing fine particles using a dehumidifying agent.

The drying unit has advantages and disadvantages according to the drying method thereof. Although a drying unit operating on the basis of dispersion using a dehumidifying agent has advantages, such as a simple structure and ease of fabrication, there is inconvenience in that the dehumidifying agent must be periodically replaced, since the performance of the dehumidifying agent is deteriorated when used for a predetermined time or longer. In particular, during a time of high humidity, such as the rainy season, or in a high-humidity location, such inconvenience further increases. When a replacement time for the dehumidifying agent is not correctly determined, the accuracy of particle measurements may be significantly lowered.

RELATED ART DOCUMENT

Patent Document 1: Korean Patent No. 10-1606561

BRIEF SUMMARY

Various aspects of the present disclosure provide a particle measuring system and, more particularly, to a particle measuring system including two drying units, in which one drying unit serves to dry fine particles, and the other drying unit serves to regenerate a dehumidifying agent, so that the dehumidifying agent can be regenerated and used semi-permanently without being replaced with a replacement and may be used more conveniently without the inconvenience of a dehumidifying agent replacing operation, and the continuity and accuracy of a measurement result can be improved.

Also provided is a particle measuring system including two drying units, in which one drying unit is provided with dry air, discharged from the other drying unit, using regenerative drying means to perform regeneration, so that the regeneration function can be simply performed without a complicated additional apparatus, and energy can be efficiently used by using the discharged dry air. Accordingly, the particle measuring system can have a simple structure and high energy efficiency.

Also provided is a particle measuring system including two drying units, in which the two drying units are provided with heaters that can be used as regenerative drying means, so that a regeneration operation of the drying unit can be more rapidly performed. In addition, when the drying units dry fine particles, the temperature of ambient air can be adjusted using the heaters, so that the accuracy of a fine particle measurement can be further improved.

According to an aspect, a particle measuring system may include: first and second drying units respectively including a main inlet and a main outlet provided on both end portions, through which fine particles in the form of aerosols are introduced and discharged, a main passage provided in a central portion to communicate with the main inlet and the main outlet, and a dehumidifying agent accommodated in an inner space of the drying unit and having a shape surrounding the main passage to dry fine particles passing through the main passage; an ambient air supply operating to selectively supply fine particles, together with ambient air, to one drying unit of the first and second drying units; a particle detector detecting fine particles discharged from one drying unit of the first and second drying units; regenerative drying means for selectively drying and regenerating the dehumidifying agent accommodated in the first drying unit and the dehumidifying agent accommodated in the second drying unit; and a controller controlling operations of the ambient air supply and the regenerative drying means. The controller controls the operation of the ambient air supply to supply fine particles and ambient air to one drying unit of the first and second drying units while controlling the operation of the regenerative drying means to dry and regenerate the dehumidifying agent accommodated in the other drying unit of the first and second drying units.

The particle measuring system may further include: a main discharge line including first and second branch lines branched from an upstream end and connected to the main outlets of the first and second drying units, such that fine particles, discharged from the first and second drying units, pass along the main discharge line; and a main pump connected to an intermediate section of the main discharge line to create flows of fine particles and air. The particle detector may be connected to the intermediate section of the main discharge line to detect fine particles.

The particle measuring system may further include: an inlet temperature and humidity sensor measuring temperatures and moisture of ambient air entering the main inlets of the first and second drying units; and an outlet temperature and humidity sensor measuring temperatures and moisture of ambient air exiting the main outlets of the first and second drying units. The controller may receive measurement values from the inlet temperature and humidity sensor and the outlet temperature and humidity sensor to control the operations of the ambient air supply and the regenerative drying means.

The controller may determine drying performance of one drying unit, of the first and second drying units, to which fine particles are being currently supplied, on basis of the measurement values of the inlet temperature and humidity sensor and the outlet temperature and humidity sensor. When the drying performance is determined to be equal to or lower than a reference level, the controller may change the operation of the ambient air supply, so that fine particles are supplied to the other drying unit of the first and second drying units, and change the operation of the regenerative drying means to dry and regenerate the dehumidifying agent contained in one drying unit, to which no fine particles are supplied in response to the changing of the operation of the ambient air supply.

The regenerative drying means may include an air circulation supply connected to a downstream end of the main discharge line to supply dry air, discharged from one drying unit of the first and second drying units, to the other drying unit. The first and second drying units may be configured such that the dehumidifying agent accommodated therein to be dried and regenerated by dry air supplied by the air circulation supply.

Each of the first and second drying units may include a dry inlet and a dry outlet in both end portions, the dry inlet and the dry outlet allowing dry air supplied by the air circulation supply to enter and exit each of the first and second drying units, and communicating with the main passage.

The air circulation supply may include: a three-way valve connected to the downstream end of the main discharge line; a first air circulation line extending from the three-way valve to the dry inlet of the first drying unit; and a second air circulation line extending from the three-way valve to the dry inlet of the second drying unit. The controller may change inner passages of the three-way valve, so that dry air, discharged from the main discharge line, is supplied via the first air circulation line or the second air circulation line.

The regenerative drying means may further include heaters disposed in the main passages of the first and second drying units to emit heat. The operations of the heaters may be controlled by the controller.

Each of the heaters may be a quartz tube heater in which a heating coil is sealed in a quartz tube.

The controller may control operations of the heaters so that one of the heaters disposed in one drying unit of the first and second drying units generates heat at a relatively-high temperature to dry and regenerate the dehumidifying agent and the other heater disposed in the other drying unit of the first and second drying units generates heat at a relatively-low to adjust a temperature of ambient air.

The ambient air supply may include: a three-way valve, to one portion of which a sampling line is connected, such that ambient air containing fine particles enters the three-way valve along the sampling line; a first ambient air supply line extending from the three-way valve to the main inlet of the first drying unit; and a second ambient air supply line extending from the three-way valve to the main inlet of the second drying unit. The controller may change inner passages of the three-way valve so that fine particles and ambient air, introduced through the sampling line, are supplied along one of the first ambient air supply line and the second ambient air supply line.

Each of the first and second drying units may include: an upper body in a top end portion of which the main inlet is provided; a lower body in a bottom end portion of which the main outlet is provided; and a central body connected between the upper body and the lower body, with a hollow mesh pipe being disposed in the central portion of the central body to define the main passage, wherein the mesh pipe includes a mesh allowing fine particles to pass through a sidewall, and is accommodated in the center case while surrounding an outer portion of the mesh pipe.

According to the present disclosure, two drying units are provided, in which one drying unit serves to dry fine particles, and the other drying unit serves to regenerate a dehumidifying agent. Accordingly, the dehumidifying agent can be regenerated and used semi-permanently without being replaced with a replacement and may be used more conveniently without the inconvenience of a dehumidifying agent replacing operation, and the continuity and accuracy of a measurement result can be improved.

One of the drying units is provided with dry air, discharged from the other drying unit, using regenerative drying means to perform regeneration, so that the regeneration function can be simply performed without a complicated additional apparatus, and energy can be efficiently used by using the discharged dry air. Accordingly, the particle measuring system can have a simple structure and high energy efficiency.

In addition, the two drying units are provided with heaters that can be used as regenerative drying means, so that a regeneration operation of the drying unit can be more rapidly performed. In addition, when the drying units dry fine particles, the temperature of ambient air can be adjusted using the heaters, so that the accuracy of a fine particle measurement can be further improved.

DETAILED DESCRIPTION

Figure 1:
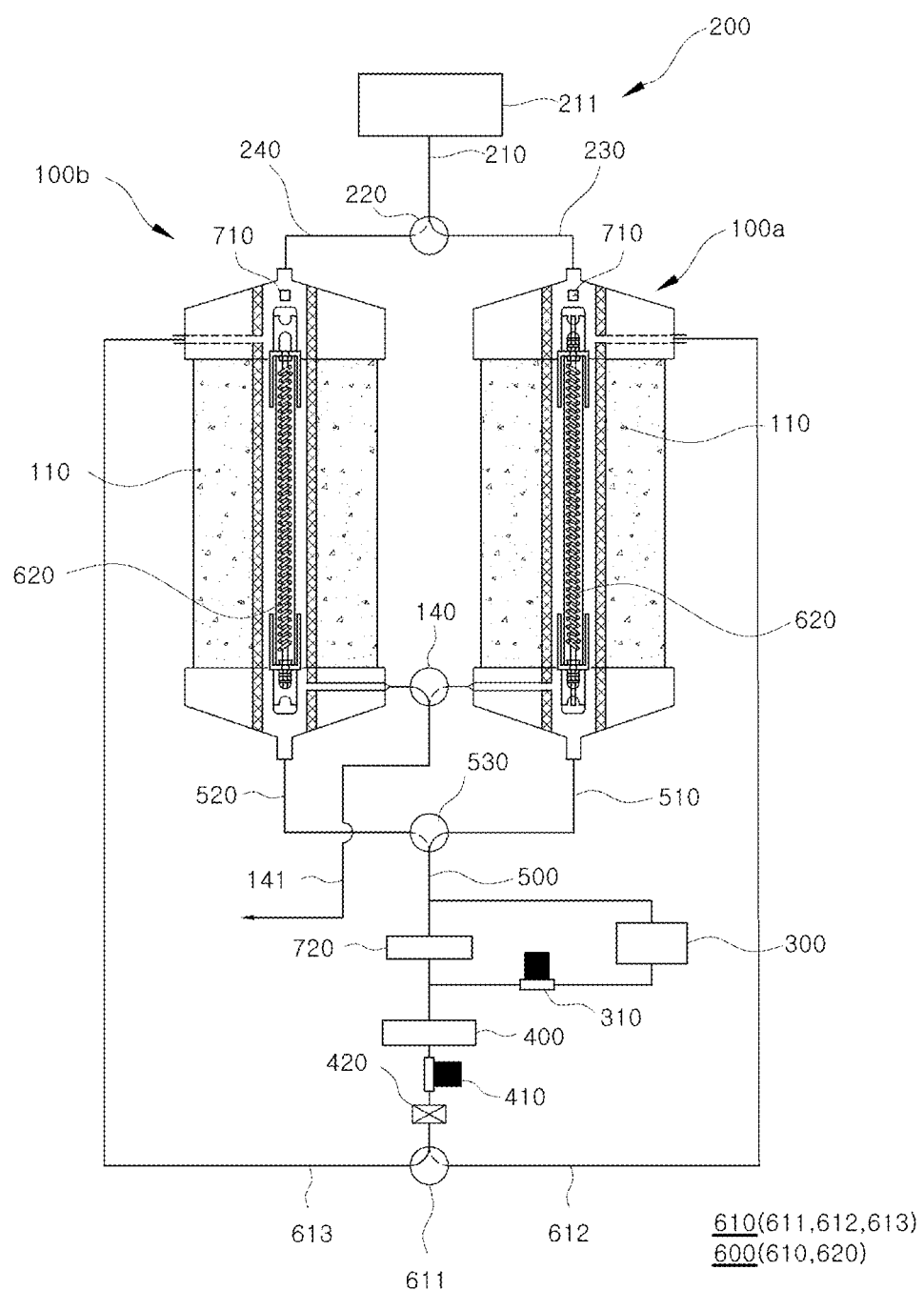
FIG. 1 is a schematic view illustrating a configuration of a particle measuring system according to exemplary embodiments.
Figure 2:
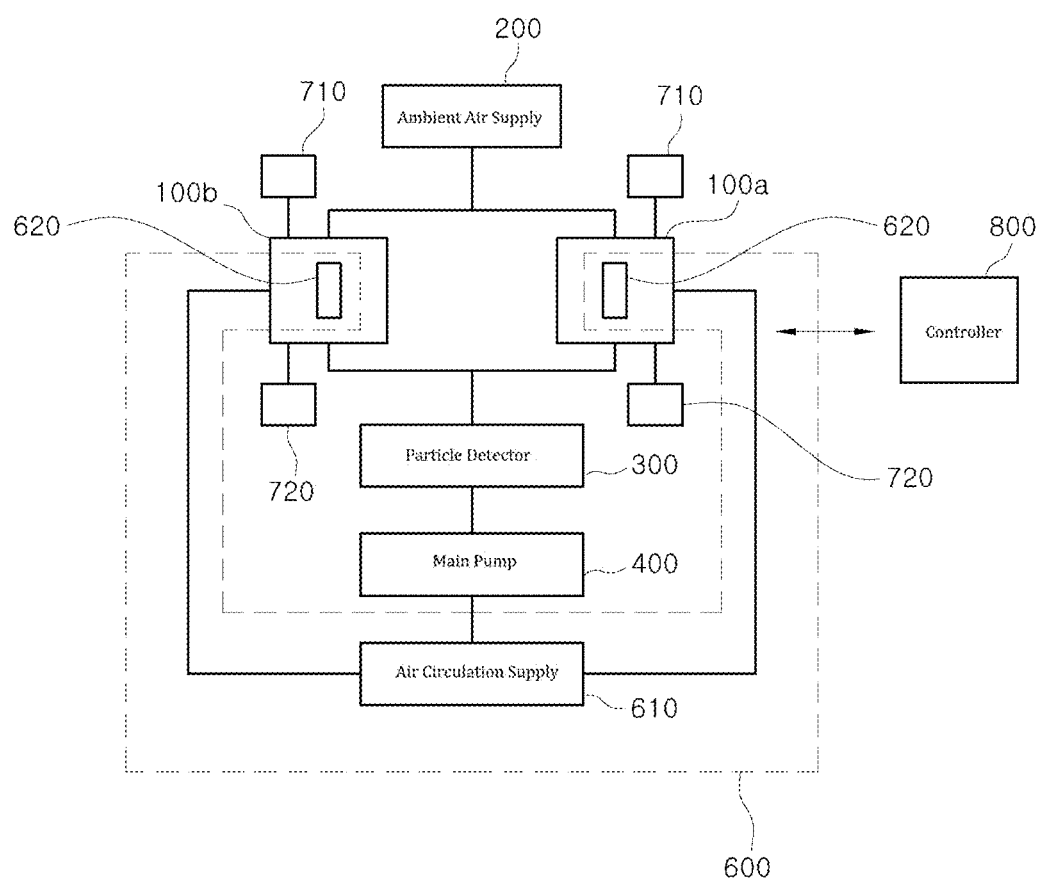
FIG. 2 is a functional block diagram illustrating the configuration of the particle measuring system according to exemplary embodiments.
Figure 3:
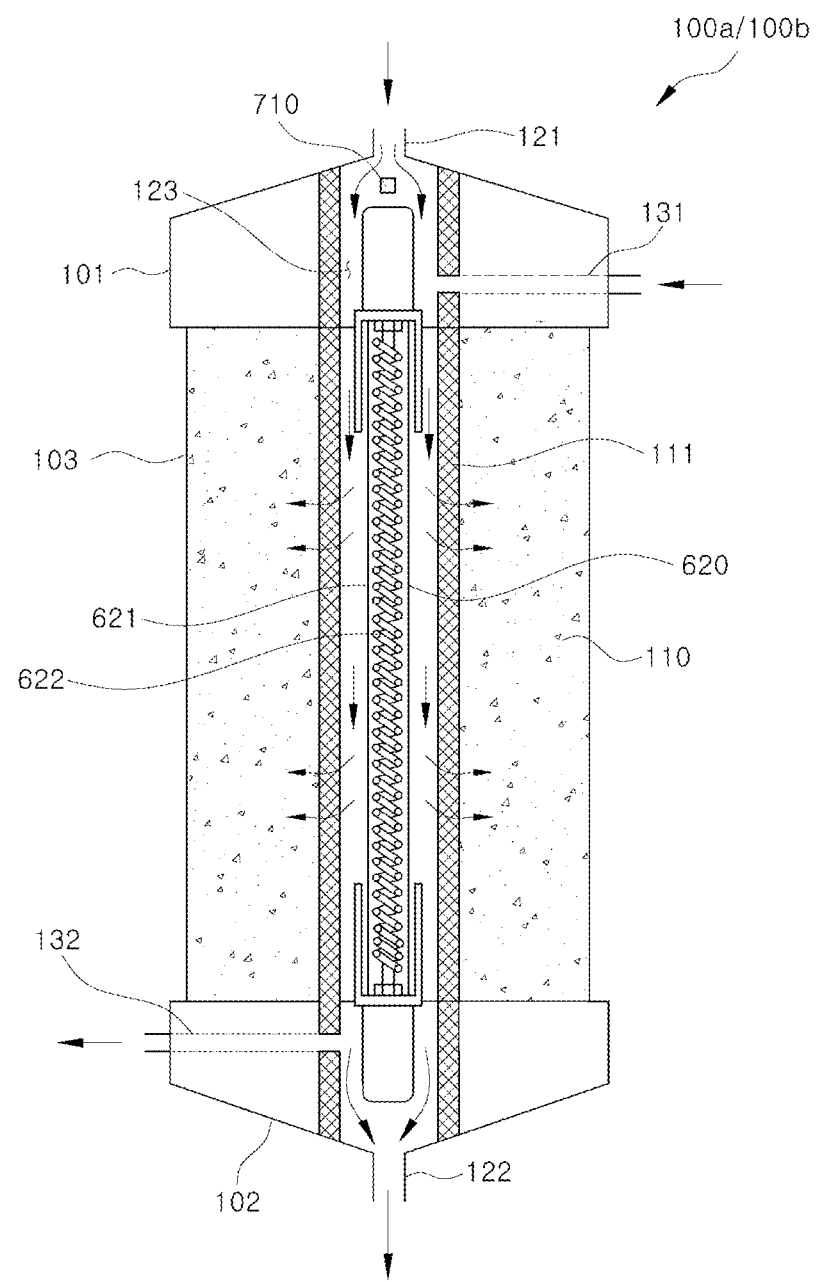
FIG. 3 is a schematic view illustrating a configuration of the drying unit of the particle measuring system according to exemplary embodiments.
Figure 4:
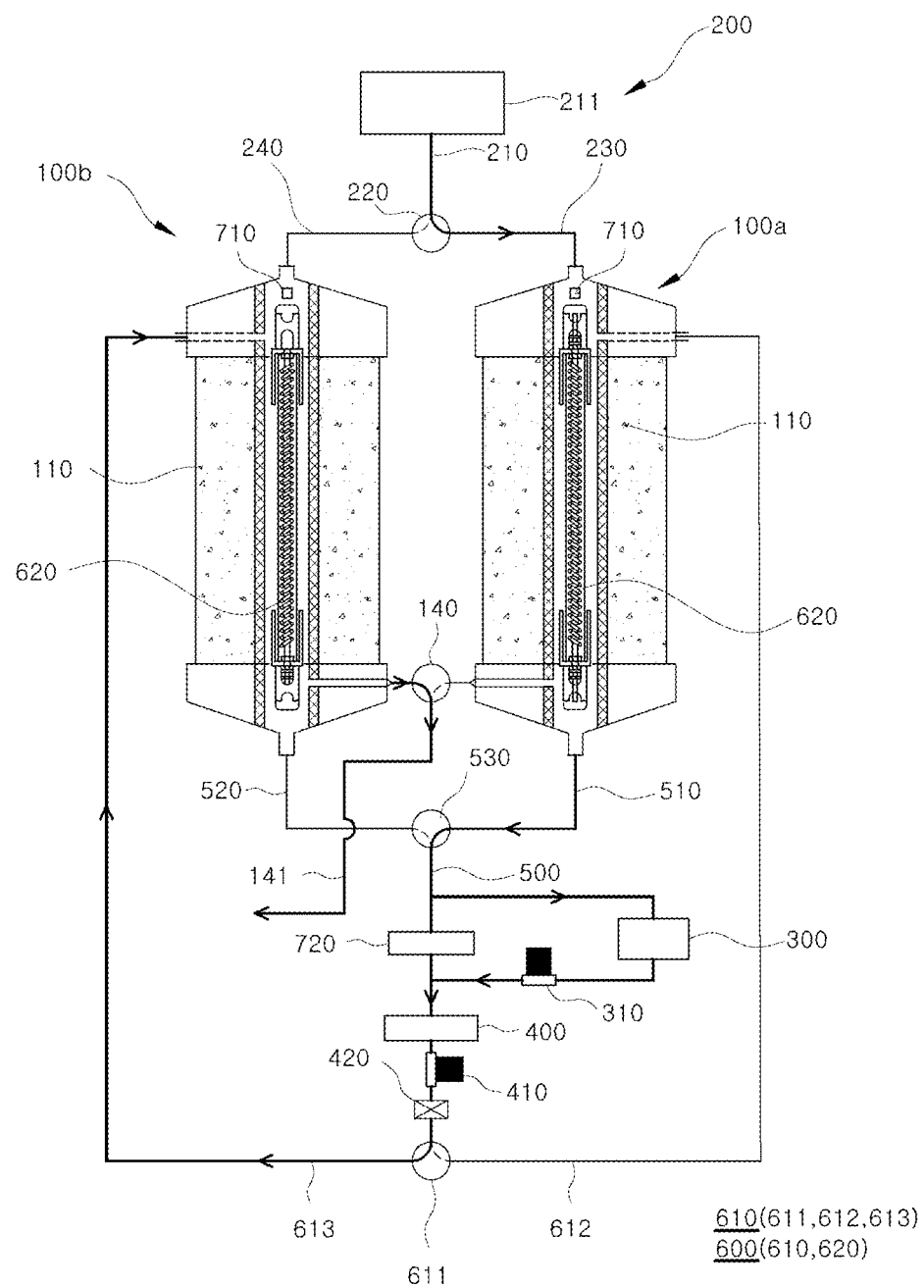
FIGS. 4 and 5 are schematic views illustrating changed states in the operation of the particle measuring system according to exemplary embodiments.
Figure 5:
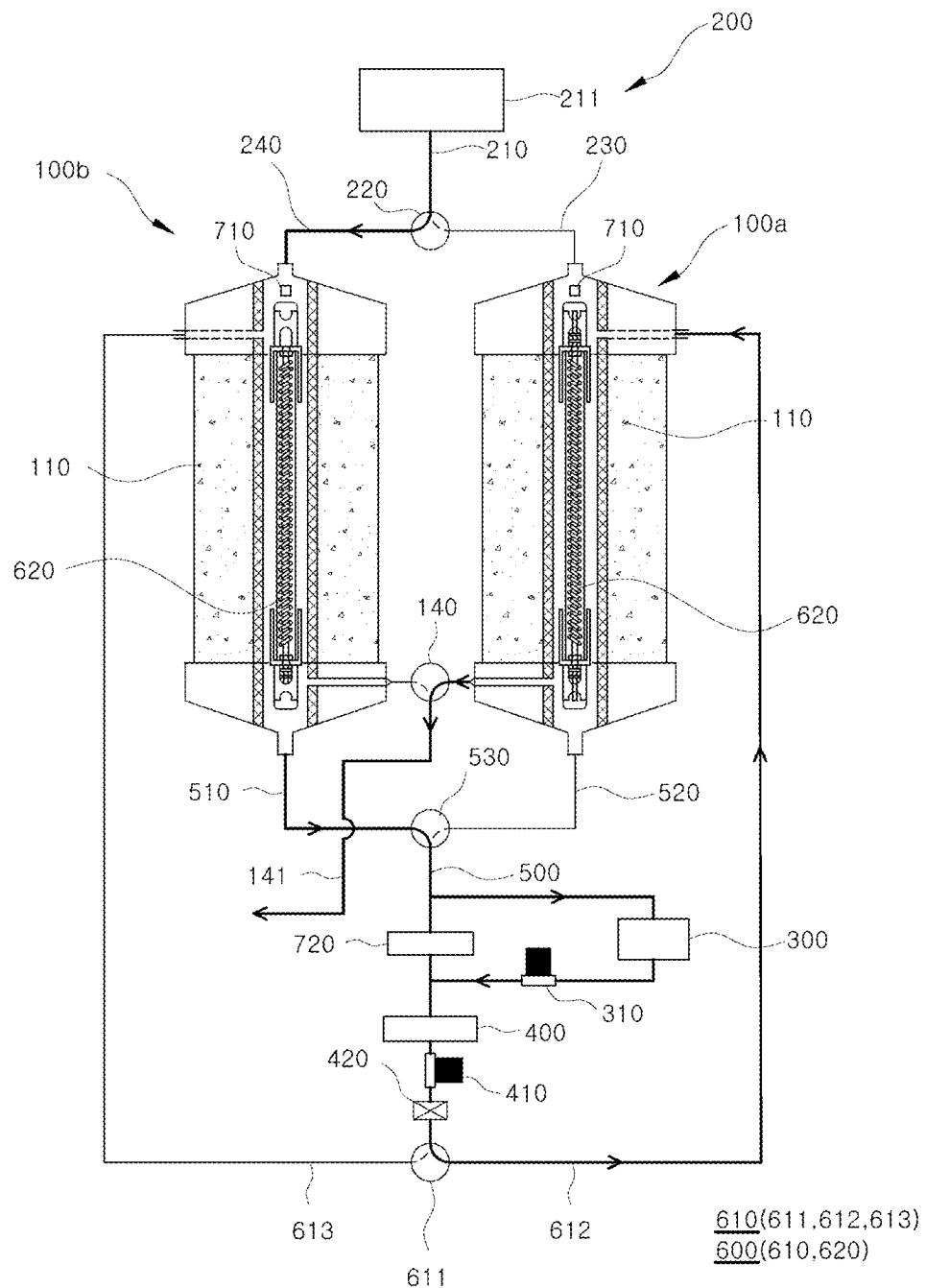

FIG. 1 is a schematic view illustrating a configuration of a particle measuring system according to exemplary embodiments, FIG. 2 is a functional block diagram illustrating the configuration of the particle measuring system according to exemplary embodiments, FIG. 3 is a schematic view illustrating a configuration of the drying unit of the particle measuring system according to exemplary embodiments, and FIGS. 4 and 5 are schematic views illustrating changed states in the operation of the particle measuring system according to exemplary embodiments.

A particle measuring system according to exemplary embodiments is a system in which the replacement cycle of a dehumidifying agent is significantly reduced or in which the dehumidifying agent can be used semi-permanently, without being replaced. The particle measuring system includes first and second drying units 100a and 100b, an ambient air supply 200, a particle detector 300, regenerative drying means 600, and a controller 800.

The first and second drying units 100a and 100b have the same configuration to perform drying by dispersion. Each of the first and second drying units 100a and 100b includes: a main inlet 121 and a main outlet 122 provided on both end portions, through which fine particles in the form of aerosols (hereinafter, referred to as aerosol fine particles) are introduced and discharged; a main passage 123 provided in the central portion to communicate with the main inlet 121 and the main outlet 122; and a dehumidifying agent 110 accommodated in an inner space of the drying unit and having a shape surrounding the main passage 123 to dry aerosol fine particles passing through the main passage 123.

The configuration of the first and second drying units 100*a* and 100*b* will be described in more detail. Each of the first and second drying units 100*a* and 100*b* may further include: an upper body 101 in the top end portion of which the main inlet 121 is provided; a lower body 102 in the bottom end portion of which the main outlet 122 is provided; and a central body 103 connected between the upper body 101 and the lower body 102, with a mesh pipe 111 in the shape of a hollow pipe being disposed in the central portion of the central body 103 to define the main passage 123.

The mesh pipe 111 is provided in the shape of a mesh allowing aerosol fine particles, flowing along the main passage 123, to pass through a sidewall. The dehumidifying agent 110 is accommodated in the central body 103 while surrounding an outer portion of the mesh pipe 111. Aerosol fine particles are dried by the dehumidifying agent 110 surrounding the mesh pipe 111 while aerosol fine particles are flowing along the main passage 123.

The ambient air supply 200 operates to selectively supply aerosol fine particles, together with the ambient air, to one of the first and second drying units 100*a* and 100*b*.

The ambient air supply 200 includes: a three-way valve 220, to one portion of which a sampling line 210 is connected, such that ambient air containing fine particles enters the three-way valve 220 along the sampling line 210; a first ambient air supply line 230 extending from the three-way valve 220 to the main inlet 121 of the first drying unit 100*a*; and a second ambient air supply line 240 extending from the three-way valve 220 to the main inlet 121 of the second drying unit 100*b*.

A sampling device 211 may be connected to a distal end of the sampling line 210. The sampling device 211 is able to supply fine particles to the ambient air supply 200. The sampling device 211 may be implemented using one of a variety of devices able to supply fine particles in the form of aerosols together with ambient air, such as a particle generator for generating particles for an experiment and a device for intaking particles from the atmosphere or from a specific location, such as a factory.

In the ambient air supply 200, one of the first and second ambient air supply lines 230 and 240 can be selected in response to the changing of inner passages of the three-way valve 220, so that fine particles and ambient air, entering through the sampling line 210, are supplied to the first drying unit 100*a* along the first ambient air supply line 230 or to the second drying unit 200*a* along the second ambient air supply line 240. The operation of changing the inner passages of the three-way valve 220 may be performed under the control of the controller 800.

The particle detector 300 is configured to detect fine particles discharged from one of the first and second drying units 100*a* and 100*b*. The particle detector 300 may be implemented using one of a variety of devices able to measure sizes and numbers of particles, such as a light scattering particle sensor.

A main discharge line 500 is connected to the main outlets 122 of the first and second drying units 100*a* and 100*b*, such that aerosol fine particles pass along the main discharge line 500. The particle detector 300 is connected to an intermediate portion of the main discharge line 500 and is configured to detect fine particles. A flow meter is disposed on a downstream end of the particle detector 300 to adjust a flow rate of fine particles entering the particle detector 300.

An upstream end portion of the main discharge line 500 is branched into first and second branch lines 510 and 520, which are connected to the first drying unit 100*a* and the second drying unit 200*a*, respectively. A three-way valve 530 is disposed on a joint in which the first and second branch lines 510 and 520 meet each other. It is possible to select one of the first drying unit 100*a* and the second drying unit 200*a* by changing inner passages of the three-way valve 530, so that fine particles and air, discharged from the first drying unit 100*a* or the second drying unit 200*a*, flow to the main discharge line 500.

In addition, a main pump 400 may be connected to the intermediate section of the main discharge line 500, such that a flow of fine particles and air is created in the entire system by operation of the main pump 400. A flow meter 410 may be disposed on a downstream end of the main pump 400 to adjust a flow rate of the flow of fine particles and air, and a filter 420 may be disposed on a downstream end of the flow meter 410 to filter discharged fine particles.

The regenerative drying means 600 is configured to selectively perform a regenerative drying function on the dehumidifying agent 110 accommodated in the first drying unit 100*a* or the dehumidifying agent 110 accommodated in the second drying unit 100*b*. The controller 800 is configured to control the operation of the ambient air supply 200 and the regenerative drying means 600.

Here, the controller 800 can control the operation of the ambient air supply 200 so that both fine particles and ambient air are supplied to one of the first and second drying units 100a and 100b and, at the same time, control the operation of the regenerative drying means 600 so that the dehumidifying agent 110 contained in the other drying unit is dried and regenerated.

In addition, inlet temperature and humidity sensors 710 are provided to measure the temperature and humidity of ambient air entering the main inlets 121 of the first and second drying units 100a and 100b, and outlet temperature and humidity sensors 720 are provided to measure the temperature and humidity of dry air exiting the main outlets 122 of the first and second drying units 100a and 100b. The inlet temperature and humidity sensors 710 may be disposed in the inner spaces of the first and second drying units 100a and 100b to be adjacent to the main inlets 121, respectively, as illustrated in FIGS. 1 and 3, or may be disposed on the main discharge line 500, as illustrated in FIG. 1. In addition, the outlet temperature and humidity sensors 720 may be disposed in the inner spaces of the first and second drying units 100a and 100b to be adjacent to the main outlets 122, respectively.

Here, the controller 800 can receive measurement values from the inlet temperature and humidity sensors 710 and the outlet temperature and humidity sensors 720 and control the operations of the ambient air supply 200 and the regenerative drying means 600.

Described in more detail, the controller 800 determines the drying performance of one drying unit, of the first and second drying units 100a and 100b, to which fine particles are being currently supplied, on the basis of the measurement values of the inlet temperature and humidity sensor 710 and the outlet temperature and humidity sensor 720. When the determined drying performance is equal to or lower than a reference level, the controller 800 changes the operation of the ambient air supply 200, so that fine particles are supplied to the other drying unit of the first and second drying units 100a and 100b, and at the same time, changes the operation of the regenerative drying means 600 to dry and regenerate the dehumidifying agent 110 contained in one drying unit, to which no fine particles are supplied in response to the changing of the operation of the ambient air supply 200.

Accordingly, the drying function is performed in one of the drying units to dry fine particles. While the drying function is being performed, the regenerative drying function is performed in the other one of the drying units performs to dry and regenerate the dehumidifying agent 110 using the regenerative drying means 600. After a predetermined period of time, the controller 800 changes the operations of the ambient air supply 200 and the regenerative drying means 600 again, so that the regeneration function is performed in the drying unit in which the drying function has been performed and the drying function is performed in the drying unit in which the regeneration function has been performed. Since the changing of the operations is repeated at predetermined periods, the drying function is performed on fine particles in one drying unit while the regeneration function is being performed on the dehumidifying agent 110 in the other drying unit. The dehumidifying agent 110 can be repeatedly regenerated and semi-permanently used, without being replaced.

The changing of the operations of the ambient air supply 200 and the regenerative drying means 600 by the controller 800 may be simply set to be repeated at predetermined periods. Alternatively, the drying performance may be determined on the basis of measurement values of the inlet temperature and humidity sensor 710 and the outlet temperature and humidity sensor 720 of the drying unit in which fine particles are being dried, and the changing of the operations of the ambient air supply 200 and the regenerative drying means 600 may be performed based on a result of the determination.

Hereinafter, the regenerative drying means 600 according to exemplary embodiments will be described in detail.

As illustrated in FIGS. 1 and 2, the regenerative drying means 600 may include an air circulation supply 610 connected to the downstream end of the main discharge line 500 to supply dry air, discharged from one drying unit of the first and second drying units 100a and 100b, to the other drying unit.

Here, the first and second drying units 100a and 100b are configured such that the dehumidifying agent 110 accommodated therein is dried and regenerated by dry air supplied by the air circulation supply 610. For example, each of the first and second drying units 100a and 100b has a dry inlet 131 and a dry outlet 132 in both end portions, allowing dry air supplied by the air circulation supply 610 to enter and exit the drying unit. The dry inlet 131 and the dry outlet 132 communicate with the main passage 123.

The air circulation supply 610 includes a three-way valve 611 connected to the downstream end of the main discharge line 500, a first air circulation line 612 extending from the three-way valve 611 to the dry inlet 131 of the first drying unit 100a, and a second air circulation line 613 extending from the three-way valve 611 to the dry inlet 131 of the second drying unit 200a.

The controller 800 controls the operation by changing the inner passages of the three-way valve 611, so that dry air, discharged from the main discharge line 500, is supplied to the first drying unit 100a via the first air circulation line 612 or to the second drying unit 100b via the second air circulation line 613.

In addition, the regenerative drying means 600 may further include heaters 620 disposed in the main passages 123 of the first and second drying units 100a and 100b, respectively. The operations of the heaters 620 may be controlled by the controller 800.

As illustrated in FIG. 3, each of the heaters 620 may be implemented using a quartz tube heater in which a heating coil 621 generating heat in response to electric power supplied thereto is sealed in a quartz tube 622 in the shape of a hollow tube. The use of the quartz tube heater can prevent chemical modification of fine particles and reduce particles additionally created by the heater, thereby improving the accuracy of the measurement of fine particles. In addition, due to the smooth surface of the quartz tube heater, flowing fine particles can be prevented from depositing on the surface of the heater, thereby minimizing particle loss. Accordingly, more accurate measurement results can be obtained.

The operation of the particle measuring system according to exemplary embodiments will be describing with reference to the configuration as described above. First, during a first period, the ambient air supply 200 supplies ambient air and fine particles to the first drying unit 100a, as illustrated in FIG. 4. Fine particles and ambient air are dried by the dehumidifying agent 110 while passing through the main passage 123 inside the first drying unit 100a, and dried fine particles and air are discharged through the main outlet 122. Dried fine particles and air, discharged through the main outlet 122, flow along the main discharge line 500 after flowing along the first branch line 510. Fine particles are measured by the particle detector 300 in the main discharge line 500, and after filtering by the filter 420 on the downstream end, dry air enters the air circulation supply 610. In the air circulation supply 610, the three-way valve 611 directs dry air to flow along the second air circulation line 613 and enter the dry inlet 131 of the second drying unit 200a. In the second drying unit 200a, dry air entering through the dry inlet 131 flows along the main passage 123 before being discharged through the dry outlet 132. In this process, dry air regenerates the dehumidifying agent 110 of the second drying unit 200a. A regeneration discharge line 141 is connected to the dry outlet 132. A three-way valve 140 directs dry air that has passed through the second drying unit 200a to be discharged outwardly along the regeneration discharge line 141. Such flows of fine particles and air are realized by the main pump 400 disposed on the main discharge line 500.

That is, during the first period, ambient air entering the first drying unit 100a is discharged as dry air after having been dried by the dehumidifying agent 110 of the first drying unit 100a. The air circulation supply 610 supplies discharged dry air to the second drying unit 200a. Dry air removes moisture from the dehumidifying agent 110 in the second drying unit 200a, so that the dehumidifying agent 110 is regenerated, while flowing along the main passage 123 of the second drying unit 200a.

In addition to the above-described supply of dry air by the air circulation supply 610, the controller 800 turns on the heater 620 of the second drying unit 200a to generate heat in order to evaporate moisture from the dehumidifying agent 110, thereby regenerating the dehumidifying agent 110. Accordingly, the regenerative drying function on the dehumidifying agent 110 of the second drying unit 200a is more rapidly and completely carried out by supplying dry air and generating heat using the heater 620.

The operation is maintained as described above during the first period. When the drying performance of the first drying unit 100a is determined to be below the reference level, on the basis of the measurement values of the inlet temperature and moisture sensor 710 and the outlet temperature and moisture sensor 720, the operation of the ambient air supply 200 is changed and fine particles and ambient air are introduced into the second drying unit 200a, as described in FIG. 5. That is, during a second period starting after the expiration of the first period, fine particles and ambient air are supplied to the second drying unit 200a, in response to the operation of the ambient air supply 200 being changed. Since the dehumidifying agent 110 of the second drying unit 200a has been regenerated during the first period, the second drying unit 200a functions to dry fine particles and ambient air using high drying performance.

Fine particles and air, dried while passing through the second drying unit 200a, are discharged along the main discharge line 500 after having flown along the second branch line 520, as described above with reference to FIG. 4. Fine particles are detected and measured by the particle detector 300 while passing along the main discharge line 500.

In addition, the inner passages of the three-way valve 611 of the air circulation supply 610 are changed along with the changing of the operation of the ambient air supply 200. Accordingly, the air circulation supply 610 directs dry air that has passed along the main discharge line 500 to enter the first drying unit 100a, instead of the second drying unit 200a. In the same manner, dry air regenerates the dehumidifying agent 110 of the first drying unit 100a while passing through the first drying unit 100a. Here, the operations of the heaters 620 are also changed, so that the heater 620 of the first drying unit 100a operates to regenerate the dehumidifying agent 110 of the first drying unit 100a, in concert with dry air.

As the changing process as described above is continuously repeated, one drying unit performs the drying function to dry fine particles, during which period the other drying unit is regenerated. The drying units can be continuously used without replacement of the dehumidifying agent 110 in the drying units. Accordingly, it is possible to more conveniently operate the particle measuring system and improve the continuity and accuracy of measurement results.

Although the controller 800 has been illustrated as controlling the operation of the heater 620 of the drying unit, performing the regeneration function, the controller 800 may control the operation of the heater 620 of the drying unit, which is performing the drying function, to generate heat at a relatively-low temperature to adjust the temperature of ambient air.

Referring to the state illustrated in FIG. 4 by way of example, when fine particles and ambient air are being supplied to the first drying unit 100a, the heater 620 of the second drying unit 200a may generate heat at a relatively-high temperature of about 100° C. to regenerate the dehumidifying agent 110 in the second drying unit 200a, while the heater 620 of the first drying unit 100a may generate heat at a relatively-low temperature of about 30° C. to adjust the temperature of ambient air, as required.

What is claimed is:

1. A particle measuring system comprising:
   first and second drying units respectively comprising a main inlet and a main outlet provided on both end portions, through which fine particles in the form of aerosols are introduced and discharged, a main passage provided in a central portion to communicate with the main inlet and the main outlet, and a dehumidifying agent accommodated in an inner space of the drying unit and having a shape surrounding the main passage to dry fine particles passing through the main passage;
   an ambient air supply operating to selectively supply fine particles, together with ambient air, to one drying unit of the first and second drying units;
   a main discharge line comprising first and second branch lines branched from an upstream end and connected to the main outlets of the first and second drying units, such that fine particles, discharged from the first and second drying units, pass along the main discharge line;
   a main pump connected to an intermediate section of the main discharge line to create flows of fine particles and air;
   a particle detector connected to the intermediate section of the main discharge line to detect fine particles discharged from one drying unit of the first and second drying units;
   regenerative drying means for selectively drying and regenerating the dehumidifying agent accommodated in the first drying unit and the dehumidifying agent accommodated in the second drying unit; and
   a controller controlling operations of the ambient air supply and the regenerative drying means,
   wherein the controller controls the operation of the ambient air supply to supply fine particles and ambient air to one drying unit of the first and second drying units while controlling the operation of the regenerative drying means to dry and regenerate the dehumidifying agent accommodated in the other drying unit of the first and second drying units,
   the regenerative drying means comprises:

an air circulation supply connected to a downstream end of the main discharge line to supply dry air, discharged from one drying unit of the first and second drying units, to the other drying unit; and heaters disposed in the main passages of the first and second drying units to emit heat to dry and regenerate the dehumidifying agent, the first and second drying units are configured such that the dehumidifying agent accommodated therein to be dried and regenerated by dry air supplied by the air circulation supply, each of the heaters comprises a quartz tube heater in which a heating coil is sealed in a quartz tube, and the controller simultaneously operates the air circulation supply and at least one of the heaters so that the dehumidifying agent is dried and regenerated by dry air supplied by the air circulation supply and heat generated by the heater.

2. The particle measuring system according to claim 1, further comprising:

an inlet temperature and humidity sensor measuring temperatures and moisture of ambient air entering the main inlets of the first and second drying units; and an outlet temperature and humidity sensor measuring temperatures and moisture of ambient air exiting the main outlets of the first and second drying units, wherein the controller receives measurement values from the inlet temperature and humidity sensor and the outlet temperature and humidity sensor to control the operations of the ambient air supply and the regenerative drying means.

3. The particle measuring system according to claim 2, wherein the controller is configured to:

determine drying performance of one drying unit, of the first and second drying units, to which fine particles are being currently supplied, on basis of the measurement values of the inlet temperature and humidity sensor and the outlet temperature and humidity sensor; and when the drying performance is determined to be equal to or lower than a reference level, change the operation of the ambient air supply, so that fine particles are supplied to the other drying unit of the first and second drying units, and change the operation of the regenerative drying means to dry and regenerate the dehumidifying agent contained in one drying unit, to which no fine particles are supplied in response to the changing of the operation of the ambient air supply.

4. The particle measuring system according to claim 1, wherein each of the first and second drying units comprises a dry inlet and a dry outlet in both end portions, the dry inlet and the dry outlet allowing dry air supplied by the air circulation supply to enter and exit each of the first and second drying units, and communicating with the main passage.

5. The particle measuring system according to claim 1, wherein the air circulation supply comprises:

a three-way valve connected to the downstream end of the main discharge line;

a first air circulation line extending from the three-way valve to the dry inlet of the first drying unit; and a second air circulation line extending from the three-way valve to the dry inlet of the second drying unit, wherein the controller changes inner passages of the three-way valve, so that dry air, discharged from the main discharge line, is supplied via the first air circulation line or the second air circulation line.

6. The particle measuring system according to claim 1, wherein the controller controls operations of the heaters so that one of the heaters disposed in one drying unit of the first and second drying units generates heat at a relatively-high temperature to dry and regenerate the dehumidifying agent and the other heater disposed in the other drying unit of the first and second drying units generates heat at a relatively-low to adjust a temperature of ambient air.

7. The particle measuring system according to claim 1, wherein the ambient air supply comprises:

a three-way valve, to one portion of which a sampling line is connected, such that ambient air containing fine particles enters the three-way valve along the sampling line;

a first ambient air supply line extending from the three-way valve to the main inlet of the first drying unit; and a second ambient air supply line extending from the three-way valve to the main inlet of the second drying unit, wherein the controller changes inner passages of the three-way valve so that fine particles and ambient air, introduced through the sampling line, are supplied along one of the first ambient air supply line and the second ambient air supply line.

8. The particle measuring system according to claim 1, wherein each of the first and second drying units comprises:

an upper body in a top end portion of which the main inlet is provided;

a lower body in a bottom end portion of which the main outlet is provided; and a central body connected between the upper body and the lower body, with a hollow mesh pipe being disposed in the central portion of the central body to define the main passage, wherein the mesh pipe comprises a mesh allowing fine particles to pass through a sidewall, and is accommodated in the center case while surrounding an outer portion of the mesh pipe.

* * * * *